United States Patent
Guth

Patent Number: 6,090,249
Date of Patent: Jul. 18, 2000

[54] ELECTRODE MATERIAL FOR HYDROCARBON SENSORS

[75] Inventor: Ulrich Guth, Greifswald, Germany

[73] Assignee: Heraeus Electro-Nite International, Hanau, Germany

[21] Appl. No.: 09/043,519

[22] PCT Filed: Sep. 25, 1996

[86] PCT No.: PCT/EP96/04184

§ 371 Date: Jun. 24, 1998

§ 102(e) Date: Jun. 24, 1998

[87] PCT Pub. No.: WO97/12413

PCT Pub. Date: Apr. 3, 1997

[30] Foreign Application Priority Data

Sep. 25, 1995 [DE] Germany ............... 195 35 381
Sep. 18, 1996 [DE] Germany ............... 196 38 181

[51] Int. Cl.$^7$ .................................................. G01N 27/407
[52] U.S. Cl. ................... 204/421; 204/424; 204/291; 204/292; 205/787; 264/104; 427/126.3; 427/126.4; 427/126.6; 429/33; 429/218.1
[58] Field of Search .................. 204/291, 292, 204/421–429; 429/33, 218.1

[56] References Cited

U.S. PATENT DOCUMENTS 4,562,124 12/1985 Ruka .
5,128,284 7/1992 Olson et al. ............... 501/12
5,306,411 4/1994 Mazanec et al. ............... 429/33

FOREIGN PATENT DOCUMENTS

| 0 188 056 | 7/1986 | European Pat. Off. . |
| 0 411 547 | 2/1991 | European Pat. Off. . |
| 0 593 281 | 4/1994 | European Pat. Off. . |
| 26 10 699 | 1/1977 | Germany . |
| 44 06 276 | 9/1994 | Germany . |
| 07 063719 | 3/1995 | Japan . |
| WO 89 00686 | 1/1989 | WIPO . |

OTHER PUBLICATIONS

Alcock et al, "Perovskite Electrodes for Sensors", *Solid State Ionics*, vol. 51, No. 3/4, Apr., 1992, pp. 281–289.

Database WPI, Section Ch, Week 9308, Derwent Publications Ltd., London.

*Primary Examiner*—T. Tung
*Attorney, Agent, or Firm*—Seyfarth, Shaw, Fairweather & Geraldson

[57] ABSTRACT

The invention relates to an electrode material for potentiometric or amperometric electrochemical sensors with the chemical composition $Ln_{1-2}A_{1-x}B_xO_3$, where Ln is at least a lanthanide cation or a mixture of rare earth cations, A is at least a trivalent transitional material, and B is at least a trivalent or bivalent redox-stable cation.

20 Claims, No Drawings

ELECTRODE MATERIAL FOR HYDROCARBON SENSORS

The invention relates to a novel electrode material for hydrocarbon sensors, as well as a novel sensor and a procedure for its manufacture.

As is known, the concentration of nonburned fuels in oxygenous gases can be determined directly by means of sensors in the combustion gas flow which feature two electrodes on a solid electrolyte, e.g., yttrium-stabilized zirconium dioxide, which respond in different ways to the test gas. As the potential of one of the electrodes is largely determined by the equilibrium oxygen partial pressure of the gas, a voltage level between the electrodes in the same gas can be determined which is dependent on the hydrocarbon concentration. Preferably, gold and alloys of gold and platinum are used as CHx-sensitive electrodes (e.g., A. Vogel, G. Baier, V. Schüle, Sensors and Actuators 15–16 (1993) 147–150).

A disadvantage of these types of arrangements is that gold electrodes are morphologically unstable over time at the relatively high operating temperatures of the cells ($\geq 700°$ C.) and that, consequently, the developing potential is subject to changers over time. Another disadvantage is that a potential jump generally takes place with these types of electrodes when the stoichiometric ratio (of $\lambda=1$) is exceeded. In addition, the potential of these types of electrodes is dependent upon pre-treatment with respect to gas admission and temperature, so that memory effects occur, which must be eliminated by constant calibration during the use of electrodes in sensors.

As is known, the electrode material may consist of mixed oxides of the perovskite type, which are generally well-known and well-researched as an oxygen electrode, and are used as materials for electrodes which, preferably, only convert oxygen electrochemically. These types of electrodes are not known as burnable gas sensitive electrodes.

The object of the invention is to provide an electrode material for a sensor which is stable over long periods of time, as well as a sensor which is stable over long periods of time.

This object is solved by an electrode material of the invention.

Because a material with the chemical composition $Ln_{1-z}A_{1-x}B_xO_3$ is provided as the electrode material for potentiometric or amperometric, electrochemical sensors, where Ln is at least lanthanide cation or a mixture of rare earth cations, A is at least a trivalent transitional material, and B is at least a trivalent or bivalent redox-stable cation, an electrode with a perovskite structure can be provided for an electrochemical sensor which is stable over long periods of time, even is aggressive high-temperature environments, once it has been sinter-fused onto a solid electrolyte or a ceramic base material.

In this regard, particularly favorable burnable gas sensitivity is achieved (with burnable gas being generally defined as a component which is gaseous or oxidizable under the operating conditions of the sensor) if the element or the element mixture A and/or the element or the element mixture B exhibits low catalytic activity.

In this regard, it is particularly advantageous if A consists of an element or a mixture of elements from the group comprising manganese, chromium, cobalt, iron and titanium. Preferably, the element or the element mixture B is selected from the group comprising gallium, aluminum, magnesium, calcium, gadolinium, and other redox-stable rare earth elements.

In particular, it is advantageous if A is manganese or chromium or a mixture of the two and if B is an element or a mixture from the group comprising gallium, aluminum, and magnesium. An electrode material in which A is chromium and B is gallium has proven to be particularly advantageous.

Furthermore, it is advantageous if Ln is a lanthanide or a mixture of lanthanides, particularly lanthanum itself, which exhibits especially advantageous properties is relation to this invention.

The parameter x ranges from 0.001 to 0.99, particularly 0.1 to 0.9, preferable 0.1 to 0.8 or 0.2 to 0.5, with a range of 0.15 to 0.25 and, particularly, 0.19 to 0.21, having proven to be particularly advantageous.

The parameter z is either equal to 0 or ranges from 0.01 to 0.29, from 0.3 to 0.6, or from 0.19 to 0.4.

If desired, the hydrocarbon sensitivity of the electrode can be increased by selecting the parameter z in relation to compounds where z=0. Due to intentional generation of under-stoichiometry of the Ln ions, oxide ion vacancies are formed in the oxygen partial matrix of the compound. As a result, sensitivity is based on other electrode mechanisms than those appearing in compounds where z=0.

The sensitivity of the electrode is additionally increased within a range of z=0.3 to z=0.6. As z increases, the element A may be present in an oxidic phase in addition to the mixed oxide, so that the electrode as a whole exists in a mixed phase.

The element or the element mixture B can also exist heterogeneously as an oxide in addition to the mixed oxide, comprising between 0.1% and 70% of the whole.

A sensor for burnable gases based on the invention, particularly for hydrocarbons, features a solid electrolyte and at least 2 electrodes, with at least one electrode containing an electrode material with the advantageous features described above.

According to one embodiment of the invention, the second electrode has the same chemical composition as the first electrode. In this case, favorable burnable gas sensitivity is achieved by providing means for generating temperature difference between the first and the second electrode. Advantageously, the temperature difference during operation between the first and the second electrode should range from $100°$ C. to $200°$ C.

In sensors in which the chemical composition of the electrodes is not identical, the chemical composition of the second electrode is, advantageously, $Ln_{1-y}C_yDO_3$, where Ln is an defined above, C is an alkaline earth metal, and D is at least a trivalent transition metal. In particular, C is strontium. Advantageously, D is manganese and/or chromium. Ln may be a different element or a different mixture of elements in the second electrode than it is in the first electrode.

Advantageously, the parameter y ranges from 0.01 to 0.9 and, particularly, from 0.02 to 0.7, 0.05 to 0.5, 0.1 to 0.3 or 0.2 to 0.4.

A process for the manufacture of a sensor for burnable gases which employs an electrode material according to the invention comprises the following steps:

Bonding of the initial products containing Ln, A and B, preferable as $Ln_2O_3$, $A_2O_3$ and $B_2O_3$, possibly with solvents;

Conversion of the mixture at about $1,350°$ C. to $1,650°$ C. to form a conversion product;

Pulverization of the conversion products;

Production of a paste; and

Imprinting and burning the paste onto a base material.

Instead of the oxide, the initial material selected may, for example, consist of the applicable citrate or nitrate compound of the initial substances.

The base material may be a solid electrolyte. However, printing may be performed directly onto an oxide ceramic base material, such as $Al_2O_3$, and a solid electrolyte may be placed over or adjacent to the printed material. $H_2O$ and/or other organic solvents are advantageously used as solvents. Hydrophilic or hydrophobic organic solvents may be used. Safe and complete oxidation of the electrode material is guaranteed once conversion to air or oxygen has occurred. If the conversion product forms a sinter product, another annealing step may take place following pulverization of the conversation product. This ensures complete homogeneous reaction of the components. In industrial manufacturing, the component $Ln_2O_3$ may also be a mineral, such as cerite earth. A composition largely corresponding to monazite is particularly advantageous.

A sensor according to the invention or a sensor which has been manufactured according to the advantageous process may find application, in particular, as a hydrocarbon sensor for use in exhaust gas or in a combustion unit, where the combustion unit may be an internal combustion engine with internal or external combustion (particularly a spark ignition engine or a diesel engine) or a heating system, such as an oil or natural gas heating system.

In this regard, favorable hydrocarbon sensitivity may be achieved if the solid electrolyte is made of a fully stabilized $ZrO_2$ containing approximately 8 mol.-% $Y_2O_3$. As a result of dotation with $Y_2O_3$, vacancies are formed in the oxygen partial matrix of the solid electrolyte.

However, it is also possible to affix the electrodes to a solid electrolyte with a low degree of $Y_2O_3$ dotation or the corresponding proportion of another cation with low valence, e.g., Mg or Ca, i.e., one having a low concentration of vacancies.

The vacancy concentration of the initial solid electrolyte can also be reduced by means of chemical modification with equivalent or superior cations. The addition $TiO_2$ or $Nb_2O_5$ is advantageous. The use of a completely different type of solid electrolyte, conceivably NASCION, is also an option.

A detailed description of the invention follows which is base on the preparation of three exemplary electrode materials according to the invention.

EXAMPLE 1

To produce the compound $LaCr_{0.80}Ga_{0.20}O_3$, the oxides $La_2O_3$ $H_2O$, $Cr_2O_3$, and $Ga_2O_3$ weighed in terms of their stoichiometric ratios and are mixed in a ball type mill for 20 minutes. The mixture is then converted in air in a sintered corundum converter at 1400° C. for 20 hours. The resulting sinter cake is mortared and annealed at 1650° C. for 30 minutes. Complete formation of the desired product can be demonstrated by means of X-ray diffractometer images.

EXAMPLE 2

To produce the compound $LaCr_{0.80}Al_{0.20}O_3$, the oxides $La_2O_3$ $H_2O$, $Cr_2O_3$, and $Al_2O_3$ in terms of their stoichiometric ratios, mixed in a ball type mill for 20 minutes, and then converted in air in a sintered corundum converter at 1400° C. for 20 hours. The resulting sinter cake is mortared and subjected to an annealing process at 1650° C. for 30 minutes to obtain the purest possible compound.

EXAMPLE 3

To produce an oxygen-sensitive perovskite electrode, the compound $La_{0.995}Sr_{0.005}CrO_3$ is weighed in terms of the stoichiometric ratios of the oxides $La_2O_3$ $H_2O$, $Cr_2O_3$, and $SrCO_3$ and mixed in a ball type mill for 20 minutes. The mixture is then converted in air in a sintered corundum converter at 1400° C. for 20 hours. The resulting sinter cake is mortared and annealed at 1650° C. for 30 minutes.

Using a basic, electronics-compatible layering technique, such as screen printing, the electrode materials based on example 1 and example 2 can be imprinted onto a solid electrolyte and can then be used next to a so-called equilibrium electrode, such as one made of platinum.

The electrode material based on example 3 forms a mixed oxide of the perovskite type with negligible burnable gas sensitivity. It can be used in place of the platinum electrode used next to the electrodes described in example 1 and example 2. The sensors, which, according to examples 1 and 2, can be manufactured as burnable gas-sensitive electrodes, or, according to example 3, as equilibrium electrodes, show no signs of the voltage jump which occurs at $\lambda=1$ with platinum electrodes, a characteristic feature of conventional $\lambda$ sensors. Thus, we obtain a burnable gas sensitive sensor which is suitable for consistent use in the vicinity of $\lambda=1$ in the exhaust gas of an automobile engine featuring a regulated catalytic converter. The signal emitted by the sensor according to the invention is primarily dependent of the concentration of burnable gases in this exhaust gas, i.e., on hydrocarbons which have not been fully burned or after burned by the catalytic converter. The constant transition from $\lambda>1$ to $\lambda<1$ and vice-versa, which is related to the regulating processes of the engine control system, does not obstruct or only slightly obstructs the output signal of the sensors according to the invention.

It is also possible to manufacture burnable gas sensors using two completely identical burnable gas sensitive electrodes, such as $LaCr_{0.8}Ga_{0.2}O_3$, by operating the two electrodes at a temperature at which burnable gas sensitivity disappears (and at which the electrode exhibits sufficient catalytic activity). This electrode then becomes an oxygen electrode. The second electrode is operated at a temperature at which the electrode material is not yet catalytically active. Consequently, burnable gas sensitivity is retained with this type of electrode. To this end, a sensor can be manufactured in which the two electrodes are affixed to the same substrate, but in which a temperature drop is set across the sensor, thereby producing a temperature difference between the electrodes of 100 K to 150 K. This temperature drop may, in particular, be generated by a heat conductor printed onto the base material of the sensor. The advantage of this embodiment consists in the fact that both electrodes can be imprinted onto the substrate or onto the solid electrolyte in a single step of the manufacturing process.

It is also possible to apply voltage to the electrochemical cells containing the burnable gas sensitive electrodes based on example 1 or example 2, on the one hand, and the oxygen electrodes based on example 3 or a platinum electrode, thereby forcing a flow of current which is directly related to the concentration of burnable gas. This mode of operating the sensors according to the invention is known in the art and is referred to as an amperometric mode of operation.

In connection with the above description, it may be assumed that lanthanides are elements with ordinal number 57 to 71, trivalent transition metals are elements with ordinal number 21 to 28, 39, 41, 42, 44, 45; 57 to 71, 74, 76, 77, 79, and 92, and, finally, redox-stable cations are such elements as Ga, Al, Sc, Mg and Ca.

What is claimed is:

1. An electrode material for potentiometric or amperometric electrochemical sensors with the chemical composition $Ln_{1-z}A_{1-x}B_xO_3$, where Ln is at least a lanthanide cation or a mixture of rare earth cations, A is an element or a mixture of elements selected from the group consisting of Mn, Cr, and Co; B is an element or a mixture of elements selected from the group consisting of Ga, Al, and Gd; x has a value of 0.001 to 0.99; and z has a value of 0 to 0.6.

2. An electrode material of claim 1 wherein A is chromium.

3. An electrode material according to claim 1 wherein B is gallium.

4. Electrode material according to claim 1, wherein Ln is an element or a mixture of elements from the group consisting of La, Nd, Sm, Eu, Gd, Dy, Ho, Er, Tm, Yb, and Lu.

5. Electrode material according to claim 1, wherein Ln is an element or a mixture of elements from the group consisting of rare earth elements.

6. Electrode material according to claim 1, wherein Ln is La.

7. Electrode material according to claim 1, wherein x falls within a range between 0.1 and 0.9.

8. Electrode material according to claim 1 wherein x falls within range between 0.1 and 0.8.

9. Electrode material according to claim 1 wherein x falls within a range between 0.2 and 0.5.

10. Electrode material according to claim 1, wherein x falls within a range between 0.15 and 0.25.

11. Electrode material according to claim 1 wherein x falls within range between 0.19 and 0.21.

12. An electrode material according to claim 1 wherein oxides of B are present in addition to the chemical composition $Ln_{1-z}A_{1-x}B_xO_3$, within a range between 0.01 wt. % and 70 wt. % of the electrode material.

13. Electrode material according to claim 1, wherein z falls with in a range between 0.01 and 0.29.

14. Electrode material according to claim 1, wherein z falls within a range between 0.3 and 0.6.

15. Electrode material according to claim 1, wherein z falls within a range between 0.19 and 0.4.

16. Sensor for burnable hydrocarbon gases, comprising a solid electrolyte and at least two electrodes, wherein at least one electrode comprises an electrode material according to claim 1.

17. Sensor according to claim 16, wherein the second electrode has the same chemical composition as the one electrode.

18. Sensor according to one of the preceding claim 16, wherein means are provided for generation of a temperature difference between the electrodes.

19. Sensor according to claim 18, wherein the temperature difference during operation between the electrodes is 100 K to 200 K.

20. A sensor for hydrocarbon in the exhaust gas of a combustion unit, said sensor having a solid electrolyte and at least two electrodes, in which at least a first electrode of the two electrodes consists essentially of an electrode material in accordance with claim 1.

* * * * *